United States Patent
Nakamura (10) Patent No.: US 8,961,478 B2
(45) Date of Patent: Feb. 24, 2015

(54) GAS MIST PRESSURE BATHING SYSTEM

(75) Inventor: Shoichi Nakamura, Higashichikuma-gun (JP)

(73) Assignees: ACP Japan Co., Ltd., Tokyo (KE); Shoichi Nakamura, Higashichikuma-gun, Nagano (JP)

( * ) Notice: Subject to any disclaimer, the term of this patent is extended or adjusted under 35 U.S.C. 154(b) by 136 days.

(21) Appl. No.: 13/138,815

(22) PCT Filed: Jun. 12, 2010

(86) PCT No.: PCT/JP2010/059983
§ 371 (c)(1),
(2), (4) Date: Oct. 3, 2011

(87) PCT Pub. No.: WO2011/043106
PCT Pub. Date: Apr. 14, 2011

(65) Prior Publication Data
US 2012/0022432 A1  Jan. 26, 2012

(30) Foreign Application Priority Data

Oct. 9, 2009 (JP) ................. 2009-235407

(51) Int. Cl.
*A61M 35/00* (2006.01)
*A61H 33/14* (2006.01)
(Continued)

(52) U.S. Cl.
CPC ................ *A61H 33/14* (2013.01); *A61H 35/00* (2013.01); *A61M 35/00* (2013.01); *A61M 1/0088* (2013.01);
(Continued)

(58) Field of Classification Search
CPC . A61M 35/00; A61M 1/0088; A61M 1/0084; A61M 2205/3344; A61F 2013/00174; A61F 13/00; A61F 15/008; A61H 35/00; A61H 2201/025; A61H 2033/145; A61H 2201/0207; A61H 2205/06; A61H 2205/10; A61H 33/14
USPC ........... 604/289, 290, 303, 305; 251/205, 208
See application file for complete search history.

(56) References Cited

U.S. PATENT DOCUMENTS 3,826,255 A * 7/1974 Havstad et al. ........... 128/200.18
4,061,698 A * 12/1977 Thornwald .................. 261/78.2
(Continued)

FOREIGN PATENT DOCUMENTS

JP   H07-171189   7/1998
JP   2006-026022   2/2006
(Continued)

*Primary Examiner* — Tatyana Zalukaeva
*Assistant Examiner* — Andrew J Mensh
(74) *Attorney, Agent, or Firm* — Manabu Kanesaka (57) ABSTRACT

The present invention is to provide a gas mist pressure bathing system enabling to cause a gas mist to be absorbed into the skin and the mucous membrane of the living organism under an optimum condition of controlling the amounts of gas and liquid. The system comprises a gas supply means 11 for supplying carbon dioxide, oxygen, otherwise a mixed gas of carbon dioxide, oxygen or air at a density of not less than a predetermined value, a liquid supply means 21, a gas mist supply means 31 which sucks up the liquid by negative pressure owing to gas flow for causing the liquid to collide with the gas for generating the gas mist prepared by pulverizing and dissolving the gas and the liquid, a living organism covering member 51 which forms a space for sealing inside the gas mist supplied from the gas mist supply means 31, wherein a gas mist supplying pressure regulating means 41 provided for controlling supplying pressure of the gas mist in such a manner of changing communicating conditions between the inside and the outside of the gas mist supply means 31 as well as regulating an amount of taking in outside air by changing.

9 Claims, 10 Drawing Sheets

(51) Int. Cl.
*A61H 33/04* (2006.01)
*A61F 13/00* (2006.01)
*F16K 1/36* (2006.01)
*F16K 5/10* (2006.01)
*A61H 35/00* (2006.01)
*A61M 1/00* (2006.01)
*A61F 15/00* (2006.01)

(52) U.S. Cl.
CPC .......... *A61M 2205/3344* (2013.01); *A61F 13/00* (2013.01); *A61F 15/008* (2013.01); *A61H 2033/141* (2013.01); *A61H 2033/143* (2013.01); *A61H 2033/145* (2013.01); *A61H 2201/165* (2013.01); *A61H 2205/06* (2013.01); *A61H 2205/08* (2013.01); *A61H 2205/10* (2013.01); *A61H 2205/106* (2013.01); *A61H 2205/108* (2013.01); *A61H 2205/12* (2013.01)
USPC ........... 604/289; 604/290; 604/303; 604/305; 251/205; 251/208

(56) References Cited

U.S. PATENT DOCUMENTS

| 4,427,004 | A | * | 1/1984 | Miller ...................... 128/200.21 |
| 5,054,478 | A | * | 10/1991 | Grychowski et al. .... 128/200.21 |
| 5,156,776 | A | * | 10/1992 | Loedding et al. ................ 261/27 |
| 7,607,639 | B2 | * | 10/2009 | Chen et al. ..................... 251/208 |
| 7,734,158 | B2 | * | 6/2010 | Kondo et al. .................. 392/325 |
| 2004/0243026 | A1 | * | 12/2004 | Toepfer et al. ................... 601/15 |
| 2004/0244792 | A1 | * | 12/2004 | Hashiba .................... 128/200.21 |
| 2010/0288562 | A1 | * | 11/2010 | Dove et al. .................... 175/340 |

FOREIGN PATENT DOCUMENTS

| JP | 2007014482 A | * | 1/2007 |
| JP | 2007-181720 | | 7/2007 |
| JP | 2008-220661 | | 9/2008 |
| JP | U-3150690 | | 4/2009 |

\* cited by examiner

GAS MIST PRESSURE BATHING SYSTEM

RELATED APPLICATIONS

The present application is National Phase of International Application No. PCT/JP2010/059983 filed Jun. 12, 2010, and claims priority from Japanese Application No. 2009-235407, filed Oct. 9, 2009.

TECHNICAL FIELD

The present invention relates to a gas mist pressure bathing system for causing a gas mist to directly contact the skin and mucous membrane of the living organism, and in particular at a density of not less than a predetermined value, thereby to improve gas absorption efficiency into the skin and mucous membrane.

BACKGROUND ART

Conventionally, it has been known that carbon dioxide (carbonic acid anhydride: $CO_2$) has both properties of being not only soluble in water (water-soluble) but also soluble in fat (fat-soluble) and, therefore, if only contacting the skin and mucous membrane of the living organism as being mixed with water and fat, carbon dioxide penetrates under a subcutaneous layer and expands blood vessels around the parts of penetrated carbon dioxide, and it works to improve the blood circulation. By this action of accelerating the blood circulation, it displays various physiological effects such as dropping of blood pressure, improving of metabolism or accelerating to remove pain substance or waste product. Further, it has also anti-inflammation and anti-bacterial. Therefore, carbon dioxide has recently been given attentions also from viewpoints of improving health or beauty other than the purpose of medical cares.

Carbon dioxide in the tissue of the living organism works to release oxygen having been carried in combination with hemoglobin in a red blood cell. Around parts at the high density of carbon dioxide, the red blood cell releases more oxygen. Thus, supply of oxygen to cells by the red blood cell is mainly controlled by carbon dioxide. In short, being without carbon dioxide, hemoglobin remains as having been combined with oxygen and the cell becomes unable to receive oxygen. As is seen, carbon dioxide seems to be waste products resulted from action of the cell, however, it plays in fact very important roles in the living organism.

Further, recently, oxygen of the high density has also widely been known as effective in activity of metabolism, acceleration of blood circulation, fatigue recovery, or stability of blood pressure. Other than them, oxygen has effects of disinfection or sterilization by oxidation.

As a prior art for causing carbon dioxide to be absorbed into the living organism, a most broadly used technique is (1) a bathing agent generating carbon dioxide in water. Throwing this bathing agent into hot water in a bathtub, it generates carbon dioxide by reacting carbonate and acid contained in the bathing agent, and dissolves it in hot water. Carbon dioxide dissolved in hot water contacts the skin of a bathing person and penetrates his/her subcutaneous layer to display physiological effects as above mentioned.

As the prior art for causing more carbon dioxide to contact the living organism, (2) a carbon dioxide bathing device has been known. This emits and disperses carbon dioxide in hot water and dissolves it at the high density. When bathing in hot water having dissolved carbon dioxide, the skin directly contacts it like the above mentioned bathing agent.

A blood circulation accelerating device (for example, Patent Document 1) has now been disclosed, which (3) attaches a cover to the human living organism on one part of his/her surface to form a sealed space together with the surface of the living organism, and introduces carbon dioxide into the sealed space from a carbon dioxide supply means for carrying out a carbon dioxide bathing.

A carbon dioxide pressure bathing device, which is equipped with at least (4) the carbon dioxide supply means, a pressurizing means, and a covering material for covering the living organism's skin and causing carbon dioxide to contact the skin at pressure of not less than predetermined value, has been proposed by an inventor of the present invention.

As the prior art for causing oxygen to be absorbed into the living organism, (5) a high density oxygen bathing device has been known. Being similar to the carbon dioxide bathing device, this emits and disperses oxygen dioxide in hot water, in which taking a bath, oxygen is caused to directly contact the skin.

CITATION LIST

Patent Document 1: Japanese Patent Application Publication No. 07-171189

SUMMARY OF INVENTION

Problems to be Solved by the Invention

However, each of the above prior arts (1), (2) and (5) dissolves carbon dioxide or oxygen in hot water when taking the bath, and causes carbon dioxide or oxygen to be absorbed into the skin of the living organism. Accordingly, they were involved with difficult points of serving each of them only when taking the bath. In addition, since carbon dioxide is easily dissolved in water and easily dispersed from water, and even if much consuming it for dissolving in hot water, an absorption rate into the skin is never much high.

On the other hand, since the above prior arts (3) and (4) cause carbon dioxide to directly contact the living organism and if comparing with the prior arts (1) and (2), effects are high and efficiency is good. But these have not optimized to control the amounts or pressures of carbon dioxide, oxygen and the mist to be introduced into the shielding member (cover).

In view of the above mentioned problems, it is an object of the invention to provide a gas mist pressure bathing system which is possible to control the amounts, pressures and others of gas and liquid, and cause the gas mist to be absorbed through the skin and mucous membrane of the human living organism under an optimum condition.

Means for Solving the Problems

For solving the above mentioned problems, the present invention is such a system which causes carbon dioxide, oxygen, otherwise a mixed gas (called briefly as "gas" hereafter) of carbon dioxide and oxygen or air and a mist prepared by pulverizing and dissolving a liquid to directly contact the skin and mucous membrane of the living organism at a density of not less than a predetermined value, and comprises a gas supply means for supplying the gas, a liquid supply means, a gas mist supply means which sucks up the liquid by negative pressure owing to gas flow from the gas supply means to cause the liquid to collide with the gas for generating and supplying the mist (called as "gas mist" hereafter) prepared by pulverizing and dissolving the gas and the liquid, and a living organism covering member which covers the skin and mucous membrane of the living organism and forms a space for sealing inside the gas mist supplied from the gas mist supply means, and is characterized by furnishing a gas mist supplying pressure regulating means in such manners that the gas mist supply means enables communication between the inside and the outside of the gas mist supply means as well as regulates an amount of taking in outside air by changing communicating conditions.

By the way, the invention refers it as "pulverizing and dissolving" to pulverize the liquid into fine liquid drops, and cause to contact and mix with gas (carbon dioxide or oxygen, otherwise, a mixed gas of carbon dioxide and oxygen or air).

Herein, the above mentioned gas mist pressure bathing system of the invention is desirably further provided with a sensor for measuring the supplying conditions of the gas, liquid and gas mist, and control means for controlling the supplies thereof based on the measuring values of the sensor.

The gas mist supplying pressure regulating means is also sufficient to have a gas storage for leading the gas existing in the gas storage into the inside of the gas mist supply means instead of outside air. In this case, the gas within the gas storage is preferably carbon dioxide, oxygen otherwise the mixed gas (containing the gas mist) of carbon dioxide and oxygen or air.

Incidentally, the control means suitably supplies the gas mist intermittently into the living organism covering member to carryout interval pressurization thereon. Otherwise, outside air or air within the gas storage is supplied under pressure intermittently into the living organism covering member by the gas mist supplying pressure regulating means to perform interval pressurization.

It is optimum that the above mentioned liquid is any one or plural combination of water, ionic water, physiological salt solution, sterilized and purified water, or liquid containing medicines. Desirably, the above medicines are any one of menthol, vitamin E, vitamin C derivative, retinol, anesthetic, cyclodextrin, complex of photocatalyst and apatite, hyaluronic acid, coenzyme Q10, seed oil, propolith, high density carbonate spring, sodium hydrogen carbonate, anti-allergic agent, anti-inflammatory agent, anti-febrile, anti-fungus agent, anti-influenza virus, carcino-static substance, and anti-hyper tensive agent. The above liquids are preferably supplied under heated condition into the gas mist supply means.

A size of the gas mist supplied from the gas mist supply means into the living organism covering member is suitably not more than 10 μm.

The control means preferably holds pressure at 1.02 to 2.5 air pressure in the living organism covering member when taking pressure bath of the gas mist.

Further on, there may be provided an electric charge supply means for supplying charge to the mist from the gas mist supply means. At this time, the charge is preferably minus.

Desirably, the gas mist supply means has a gas mist supply pipe for supplying the gas mist into the living organism covering member, and this gas mist supply pipe is suitably composed of a cornice shaped pipe over a whole or at one part of the gas mist supply pipe. In addition, this gas mist supply pipe is provided with a check valve.

In addition, the gas mist supply inlet of the living organism covering member is also provided at its supply inlet with the check valve.

Within the gas mist supply device, it is desirable to place one or plurality of pored plates for refining the gas mist.

The control means desirably stops the gas from the gas supply means when the pressurizing value within the living organism covering member is higher than a predetermined value.

Advantageous Effects of Invention

According to the gas mist pressure bathing system of the invention, since it is possible to control the amount and pressure of the gas mist existing in the pressure bathing cover for the living organism by the control device, the gas mist pressure bathing can be always taken under the best condition.

Further, pressurization into the pressure bathing cover for the living organism is easy, and the gas can be carried out more efficiently.

DESCRIPTION OF EMBODIMENTS

In the following description, explanations will be made to the embodiments of this invention, referring to the attached drawings.

First Embodiment

Figure 1:
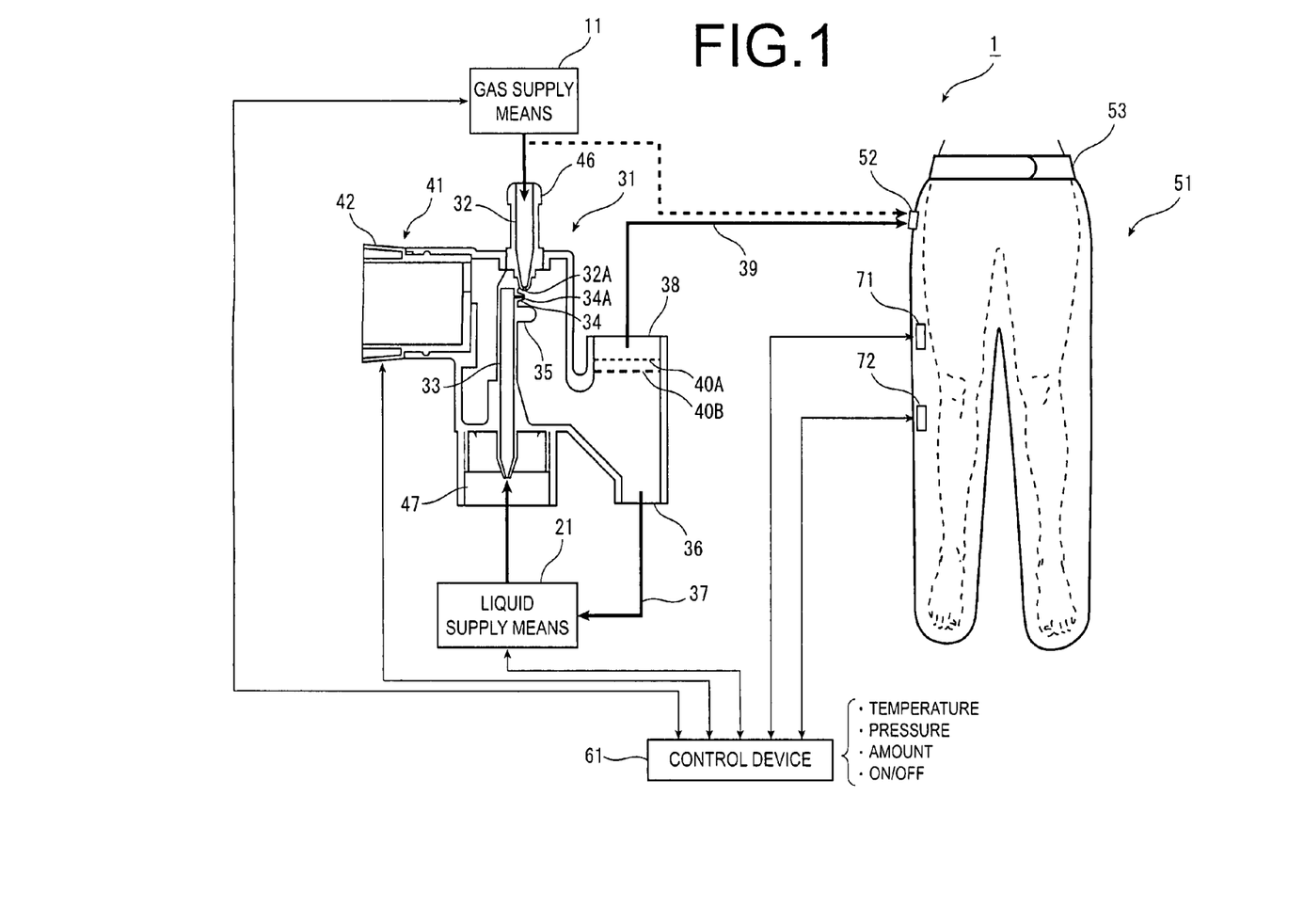
FIG. 1 A generally schematic view of the gas mist pressure bathing system depending on a first embodiment of the invention.

FIG. 1 is the generally schematic view of the gas mist pressure bathing system depending on the first embodiment of the invention. As illustrated herein, the gas mist pressure bathing system 1 depending on the present embodiment is composed of the gas supply means 11 for supplying carbon dioxide or oxygen, otherwise the mixed gas (called collectively as "gas" hereafter) of carbon dioxide and oxygen or air at the density of not less than a predetermined value, the liquid supply means 21 for supplying liquid, the gas mist supply device (gas mist supply means) 31 which generates the mist (called as "gas mist" hereafter) prepared by pulverizing and dissolving gas and liquid, and supplies under pressure, and the pressure bathing cover 51 for the living organism (the living organism covering means) which covers the living organism and forms a space for sealing inside thereof the supplied gas mist and contacting it to the living organism, and a control device (control means) 61 for controlling gas mist generation and controlling supply.

The gas supply means 11 supplies the carbon dioxide or oxygen, otherwise the mixed gas of carbon dioxide and oxygen or air to the gas mist supply means 31. As the gas supply means 11, to use a gas bomb is suitable. Omitting illustration, to the gas supply means 11, there is desirably furnished a regulator for regulating pressure of gas. Further, it is sufficient to dispose a heater (not shown) for heating gas or a temperature gauge (not shown).

The liquid supply means 21 is to supply liquid to the gas mist supply device 31. For this liquid supply means 21, such a manner may be sufficient to automatically or manually pour by the control device 61. Further on, later describing, since the gas mist supply device 31 of this invention has a structure of sucking up liquid from the liquid nozzle 33 by negative pressure occurring owing to high speed flow of gas, it is enough to employ a device such as the liquid supply means 21 which does not especially furnish a liquid pouring means. For example, a syringe or pack is suitable as sealing liquid inside thereof.

Figure 2:
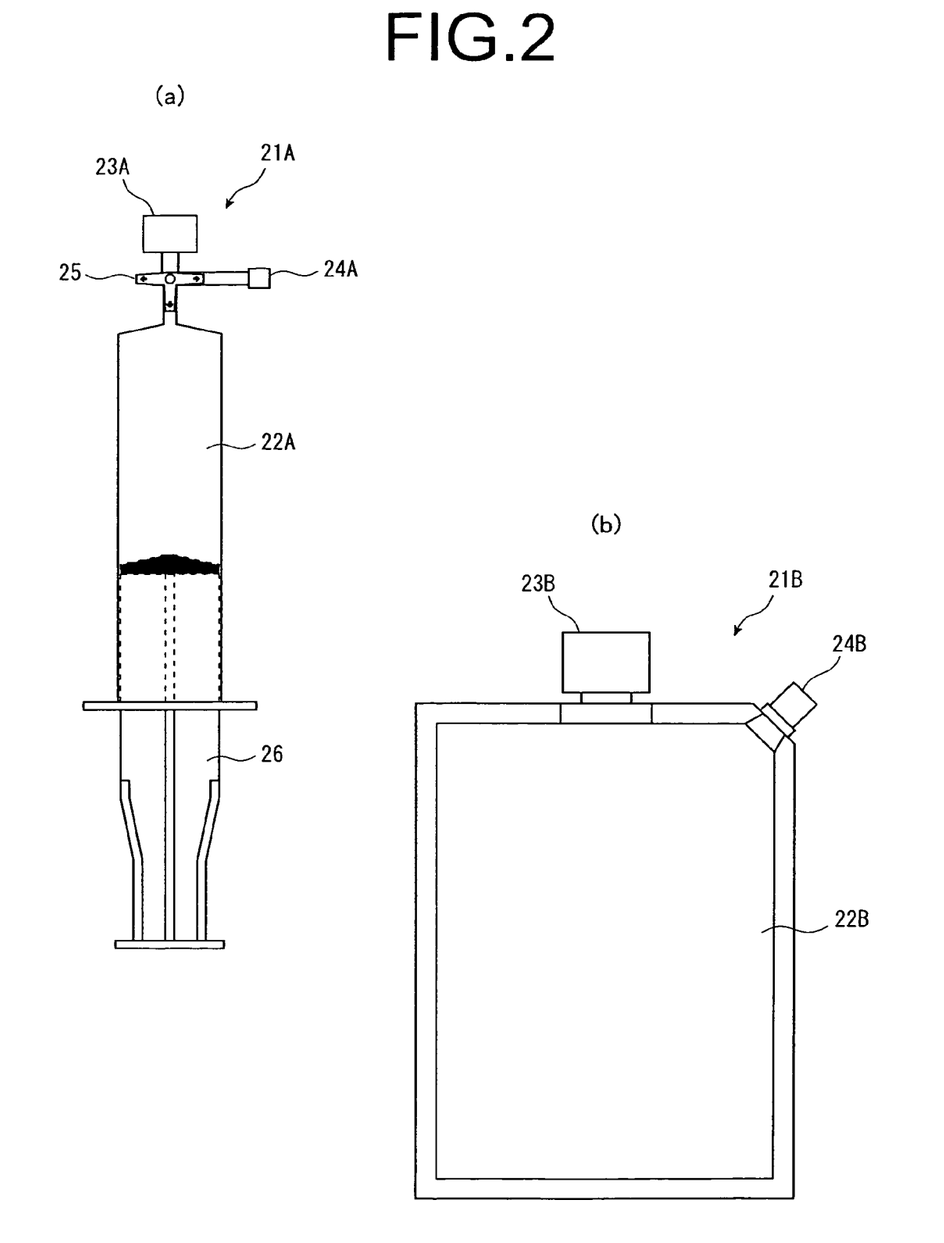
FIG. 2 Typical views showing the concrete examples of the liquid supply means of the gas mist pressure bathing system based on the invention.

FIG. 2 shows concrete examples of the liquid supply means 21. FIG. 2(a) shows the example of the syringe 21A, and FIG. 2(b) shows the example of a liquid pack 21B. As shown therein, the liquid supply means 21 has liquid storages 22A, 22B and connecting portions 23A, 23B for connecting to the gas mist supply device 31, and further the liquid supply means 21 has liquid supply inlets 24A, 24B for connecting to a later mentioned liquid discharge pipe 37. In the case of the syringe 21A, there are furnished a change valve 25 which respectively changes a flow from the liquid storage 22A to the connecting portion 23A, another flow from the liquid supply inlet 24A to the liquid storage 22A and a further flow from the liquid supply inlet 24A to the connecting portion 23A, and a piston 26 for pushing out liquid to send it to the gas mist supply device 31.

The liquid supply means 21 is desirably equipped with a heater (not shown) for heating liquid (for example, heating water to around 40° C.) or a temperature gauge (not shown). Gas may be supplied to the gas supply means under a heated condition.

Herein, the liquid supplied by the liquid supply means 21 is suitable to employ water, ionic water, ozone water, physiological salt solution, distilled water, purified water or sterilized and purified water. Further, these liquids may contain medicines useful to user's diseases or symptoms. For the medicines, enumerated are, for example, anti-allergic agent, anti-inflammatory agent, anti-febrile, anti-fungus agent, anti-influenza virus, carcinostatic substance, anti-hypertensive agent, cosmetic agent, or trichogen. Further, these liquids are possible to generate synergistic effects by coupling with a gas physiological action with single or plurality of menthol having a cooling action; vitamin E accelerating circulation of the blood; vitamin C derivative easily to be absorbed to the skin tissue and having a skin beautifying effect; retinol normalizing a skin heratinizing action and protecting the mucous membrane; anesthetic moderating irritation to the mucous membrane; cyclodextrin removing odor; photocatalysis or a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, ant-inflummatory agent, pain-killing, anesthetic, and immunity. Otherwise, the liquids may be added with ethanol, gluconic acid chlorohexizine, amphoteric surface active agent, benzalkonium chloride, alkyldiamino ether glycin acetate, sodium hypochlorite, acetyl hydroperoxide, sodium sesqui-carbonate, silica, povidone-iodine, sodium hydrogen carbonate.

The gas mist supply device 31 has a gas nozzle 32 supplied with gas from the gas supply means 11, the liquid nozzle 33 supplied with liquid from the liquid supply means 21, a liquid discharge portion 36 for discharging liquid stored within the device, a gas mist discharge outlet 38 for supplying the gas mist, and further has a regulator (gas mist supply pressure regulating means) 41 for regulating supply pressure of the generated gas mist.

The gas nozzle 32 discharges gas supplied from the gas supply means 11 from its front end open 32A, and is shaped to reduce a diameter gradually as coming toward the front end for heightening gas flow speed as shown.

The liquid nozzle 33 is supplied with liquid from the liquid supply means 21, and has a liquid sucking pipe 34 being narrow to suck up liquid by negative pressure occurring by high speed flow of gas. The liquid sucking pipe 34 has a front end open 34A nearly the front end open 32A of the gas nozzle 32, and is so composed that liquid sucked up by the liquid sucking pipe 34 collides with the gas flow discharged from the gas nozzle 32. Further, the liquid nozzle 33 has a baffle (colliding member) 35 at a position opposite to the front end open 32A of the gas nozzle 32 crossing the front end open 34A of the liquid sucking pipe 34. The gas nozzle 32 and the liquid nozzle 33 are desirably formed as one body with a material as a resin.

In case generating excessive liquid drops when generating or supplying the gas mist, the liquid discharge portion 36 is to discharge it as it is and return to the liquid supply means 21. The liquid discharge portion 36 is connected to the liquid discharge pipe 37, and this liquid discharge pipe 37 is connected to the liquid supply inlet 24A of the liquid supply means 21 as mentioned above.

The gas mist discharge outlet 38 is connected to the gas mist supply pipe 39, and supplies therefrom the gas mist into the pressure bathing cover 51 for the living organism. The gas mist generated in the gas mist supply device 31 passes from the gas mist discharge outlet 38 and the gas mist supply pipe 39 and from a later mentioned gas mist supply inlet 52 into the pressure bathing cover 51 for the living organism. The gas mist supply pipe 39 is provided inside with a check valve for preventing a back flow of the gas mist, though not showing. The gas mist supply pipe 39 may be provided with a filter for removing extra liquid drops attached to the inside of the pipe, though not showing, either.

Figure 5:
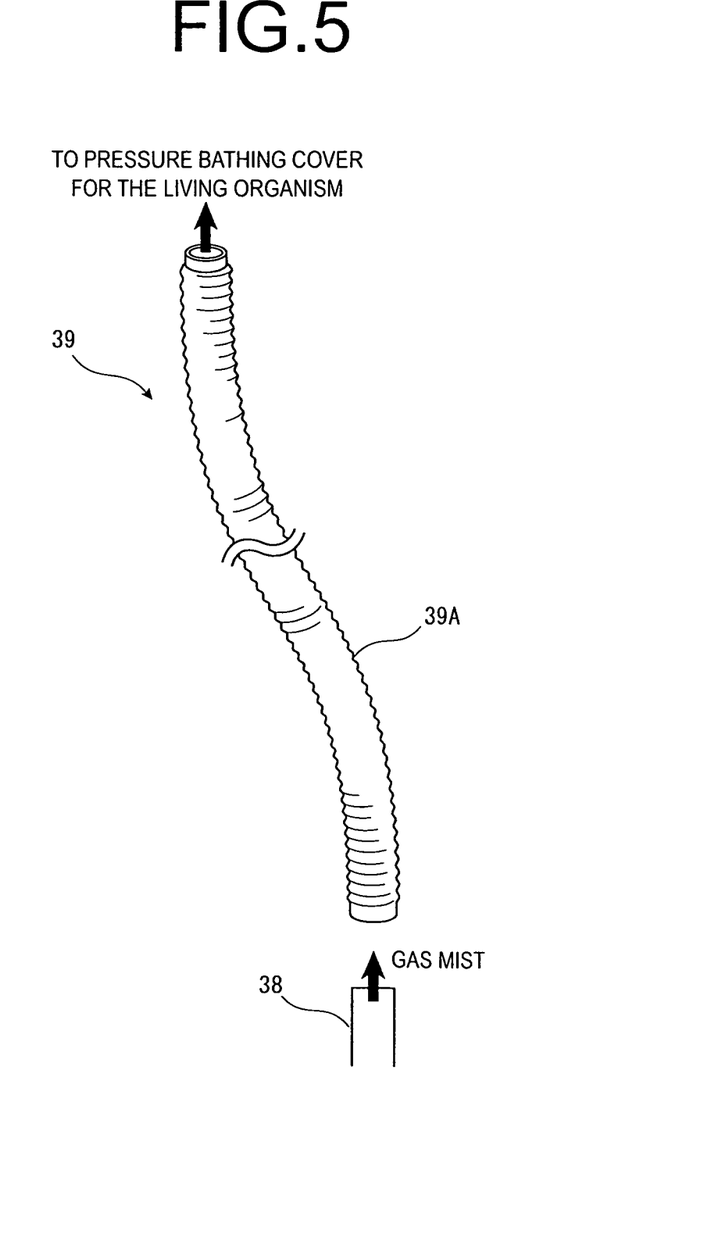
FIG. 5 A typical view showing one example of the gas mist supply pipe used to the gas mist pressure bathing system of the invention.

Further, if the gas mist supply pipe 39 is overall or partially composed of a soft cornice shaped pipe 39A of a large diameter as shown in FIG. 5, it may be freely bent and may be expanded so that a user of this system is not restricted in his actions. Even if the gas mist flowing in the gas mist supply pipe 39 becomes gradually liquefied, the liquid can be removed through the concave and convex of the cornice.

Figure 6:
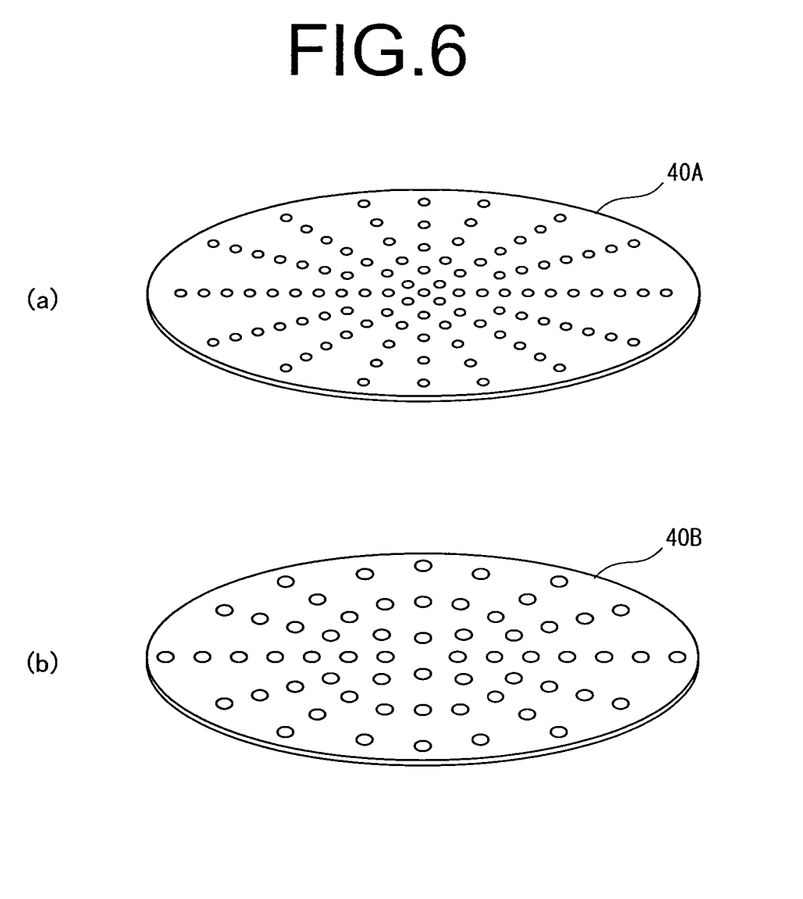
FIG. 6 Typical views showing examples of plates to be placed within the gas mist supply device of the gas mist pressure bathing system of the invention.

It is preferable to provide one sheet or plural sheets (in FIG. 1, two sheets, as an example) of plates 40A, 40B in the vicinity of the gas mist discharge outlet 38 of the gas mist supply device 31. FIG. 6 shows the examples of the plates 40A, 40B. Thus, the plates 40A, 40B are formed with plural pores, and the generated gas mist is refined when passing through these pores. With respect to the upper plate 40A and the lower plate 40B, it is preferable that the diameters of the pores of the upper plate 40A are smaller than those of the pores of the lower plate 40B. Thereby, mists of unit being micron can be obtained. The plates desirably have plural pores being radial or concentric toward extension.

Figure 3:
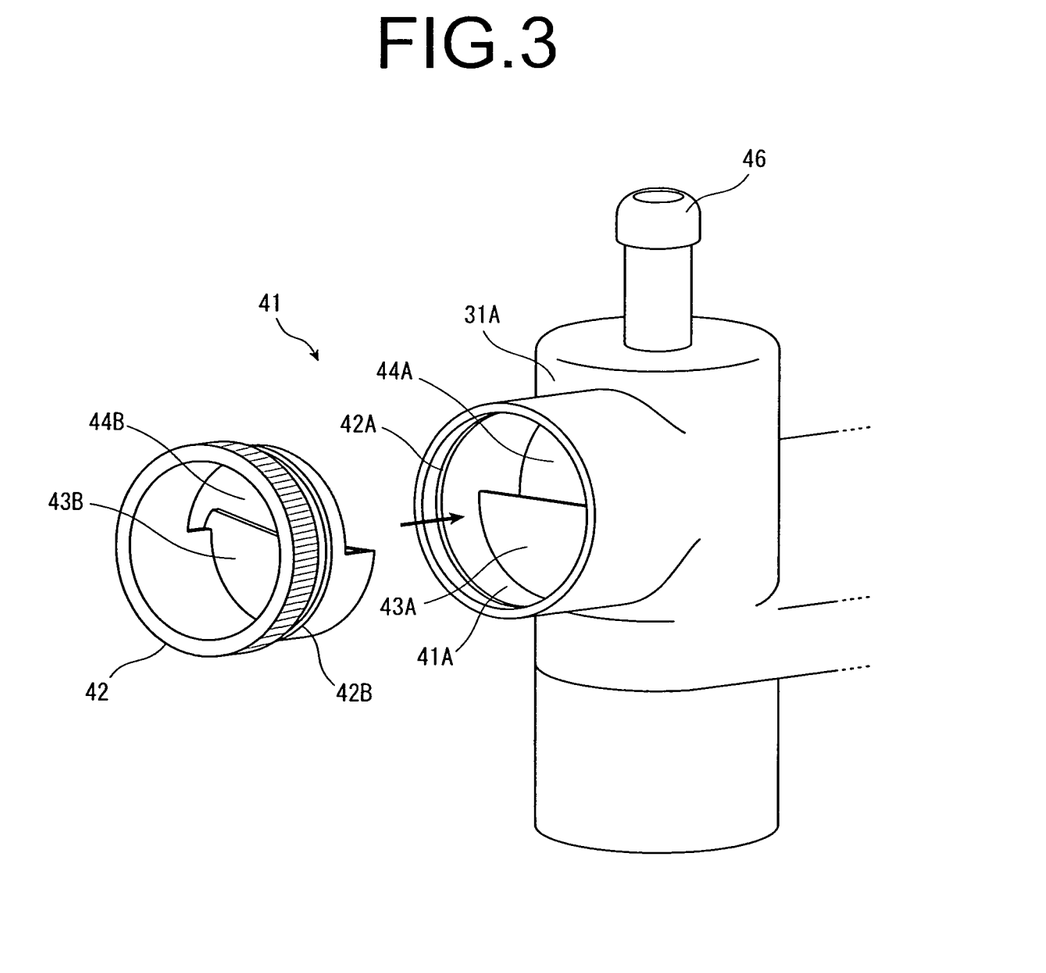
FIG. 3 Disassembled and perspective views showing a concretely structured example of the regulating part of the gas mist pressure bathing system based on the invention.

A regulator 41 is a flowing amount control valve for regulating supply pressure of the gas mist into the pressure bathing cover 51 for the living organism by regulating to take in outside air into the gas mist supply device 31. FIG. 3 shows the concrete example of a structure of the regulator 41. As shown therein, the regulator 41 is a substantially cylindrical body with a bottom, and has a rotating part 42 with one portion of the cylinder and one portion of the bottom which open almost in semicircle (opening 44B). Further, the gas mist supply device main element 31A has an engaging portion (engaging hole) 41A with which the rotating part 42 engages. The rotating part 42 and the engaging portion 41A are made rotatable in such a way that mesh is obtained between a convex portion 42B provided in the rotating part 42 and a concave grooved portion 42B provided in the inside of the engaging portion 41A. By the way, of course, combination between the convex portion and the concave grooved portion may be obtained even if the rotating part 42 and engaging portion 41A are furnished reversely. Inside of the engaging portion 41A, the semicircle 43A is disposed at a position contacting the semicircle 43B formed in the cylindrical bottom when engaging the rotating part 42 with respect to the engaging portion 41A. When closing the regulator 41, these two semicircles 43A, 43B can close a path 44A communicating to the inside space of the gas mist supply device 31. For accomplishing this purpose, the semicircles 43A, 43B not necessarily accurate, but desirably, those close the path 44A as overlapping somewhat. For opening the regulator 41, the rotating part 42 is turned in an axial direction. Then, the two semicircles 43A, 43B overlap, so that the path of outside air is formed, passing from the opening 44B and through path 44A to the gas mist supply device 31. When the regulator 41 opens, outside air is taken in by air flow within the gas mist supply device 31, and supplying pressure of the gas mist is heightened. At this time, depending upon turning angles of the rotating part 42, the communicating condition between the inside and outside of the gas mist supply device 31 is varied. That is, the larger is the overlapping condition of the semicircles 43A and 43B, an inlet of outside air becomes larger and the amount of taking in outside air becomes larger. In this manner, by controlling the rotational angle of the rotating part 42, the supplying pressure of the gas mist is controlled. This regulator 41 is desirably controlled to open and close by a later mentioned control device 61.

Figure 4:
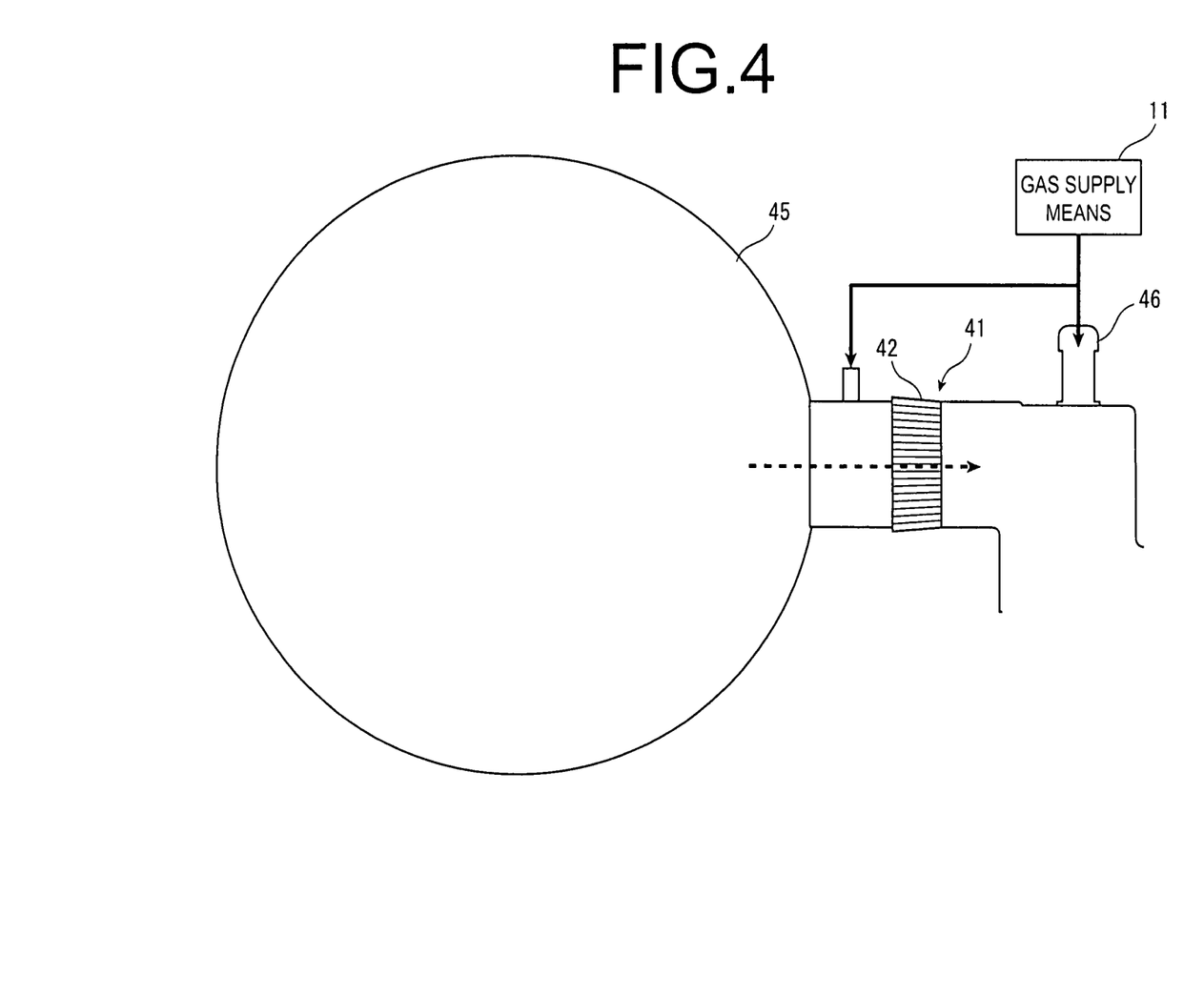
FIG. 4 A schematic view of the other structured example of the regulating part of the gas mist pressure bathing system based on the invention.

By the way, if sending outside air from the regulator 41, the density of the supplied gas mist naturally goes down. Then, as shown in FIG. 4, it is sufficient to communicate a bag shaped gas storage 45 to the rotating part 42 in order to supply gas in the gas supply means 11 instead of outside air. If having previously stored gas from the gas supply means 11 in the gas storage 45, when opening the regulator 41, gas therein is drawn into the gas mist supply device 31. At this case, for easily drawing gas, the gas storage 45 is composed of a soft material. Gas stored in the gas storage 45 may be different from gas in the gas supply means 11 (for example, from the gas supply means 11, carbon dioxide is supplied, while the gas storage 45 stores oxygen). Further, the gas storage 45 may store the gas mist.

Since pressurization in the gas mist pressure bathing heightens effects by carrying it out in pulse at predetermined intervals, the gas mist is supplied into the pressure bathing cover 51 for the living organism intermittently at a determined rhythm. Otherwise, the regulator 41 is sufficient to open and close at the determined rhythm. At this time, the pressurizing effect is heightened by synchronizing the supply of the gas mist with the stroke of the pulse or by synchronizing the opening and closing intervals with the stroke of the pulse. The supplying control and the opening and closing control of the regulator 41 are suitably carried out by the control device 61 as mentioned above.

The gas mist supply device 31 further has a gas mist supply means joint 46 for connecting to the gas supply means 11 and a liquid supply means joint 47 for connecting to the liquid supply means 21.

The pressure bathing cover 51 for the living organism is a cover which enables to form a space for covering the skin and mucous membrane of the living organism (herein, as the example, a lower extremity of the living organism) and to seal the gas mist inside. The pressure bathing cover 51 for the living organism is composed of a water resistant, non-air permeable and non-moisture permeable material, for example, preferably, the natural rubber, silicone rubber, polyethylene, poly-propylene, polyvinylidene, poly stylene, polyvinylacetate, polyvinyl chloride, polyamide resin, polytetrafluoroethylene. The pressure bathing cover 51 for the living organism has a supply inlet 52 for introducing the gas mist inside. The supply inlet 52 is inside provided with a check valve for blocking back flow of the gas mist. The pressure bathing cover 51 of the living organism may be provided with an open exit or a valve for exhausting the gas mist in order to control inside pressure. The pressure control may be carried out manually, but desirably automatically by a control device 61 together with supply control of the gas mist on the basis of measuring values of a later mentioned manometer 71. A safety valve (recess valve) may be provided for automatically opening the valve when the inside of the pressure bathing cover 51 becomes more than a constant pressure.

The pressure bathing cover 51 for the living organism is inside installed with the manometer 71 for measuring internal pressure. The control device 61 controls supply of the gas mist on the basis of measuring values of the manometer 71 for maintaining a pressure value within the pressure bathing cover 51 for the living organism to be more than 1 air pressure (more preferably, around 1.02 to 2.5 air pressure). For example, supply of the gas from the gas supply means 11 is turned on or off, opening angles of the regulator 41 are controlled, or the gas mist is exhausted from the pressure bathing cover 51 for the living organism. Further, the pressure bathing cover 51 for the living organism is inside installed with a temperature gauge 72 for measuring a temperature within the pressure bathing cover 51 for the living organism. The control device 61 performs on-off of a heater installed in the liquid supply means 21 on the basis of measuring values of the temperature gauge 72 for maintaining a determined temperature (for example, around 38° C.) bringing about warm bath effects within the pressure bathing cover 51.

The pressure bathing cover 51 for the living organism has, around its opening, a stopper 53 for attaching to and detaching from the living organism (herein, as the example, the lower extremity of the living organism) and for preventing leakage of the gas mist. The stopper 53 is suitably composed of, e.g., a face fastener of stretching property, or may have a sole, string, rubber or their combination. For heightening a sealing property of the pressure bathing cover 51, the inside (such as an inside of the stopper 53) of the pressure bathing cover 51 may have a material attaching to the user's skin. The adhesive material is preferably, for example, a visco-elastic gel made of polyurethane or silicone rubber. Further this adhesive material is detachably used and exchangeable each time or if viscosity becomes weak.

The control device 61 is composed of a computer having CPU, memory and display. This device 61 performs various kinds of controls for carrying out the gas mist pressure bath under the optimum condition, such as pressure or temperature controls, on-off switch of the gas supplied from the gas supply means 11, temperature control of the liquid of the liquid supply means 21, on-off switch of liquid pouring, or open-close switch of the regulator 41 of the gas mist supply device 31. In particular, preferably, when the pressure value becomes more than a predetermined value in the pressure bathing cover 51 for the living organism, such a structure is composed to stop supplying the gas from the gas supply means 11 by the control device 61.

For carrying out the gas mist pressure bathing by using the gas mist pressure bathing system 1 of the present embodiment, the pressure bathing cover 51 is fixedly secured to the living organism (herein, as the example, the lower extremity of the living organism) and closed. Gas is supplied from the gas supply means 11 into gas mist supply device 31, and is exhausted from the gas nozzle 32. Then, the liquid is sucked up by negative pressure generated owing to air current, reaches the liquid sucking pipe 34 from the liquid nozzle 33, runs against the gas flow at the front end open 34A of the liquid sucking pipe, and collides with the baffle 35. By this collision, the gas mist is generated. The control device 61 performs controls of gas supplying pressure or liquid temperature. If necessary, the regulator 41 is opened and closed to regulate gas mist supplying pressure. A size of the mist then generates is desirably fine, and concretely, less than 10 μm is optimum.

The generated gas mist passes through the fine holes of the plates 40A, 40B and reaches the gas mist supply pipe 39 from the gas mist discharge outlet 38. The mist liquefied then is exhausted from the liquid discharge portion 36 into the liquid discharge pipe 37 and is returned the liquid supply means 21. The gas mist having reached the gas mist supply pipe 39 is supplied into the pressure bathing cover 51 for the living organism from the gas mist supply inlet 52. At this time, preferably, in the pressure bathing cover 51 for the living organism, the gas is controlled to exist about 95 to 97%, while the liquid is controlled to exist about 3 to 5%. The control device 61 is controlled such that the inside of the pressure bathing cover 51 for the living organism becomes an optimum pressurized and heated condition (around 1.02 to 2.5 air pressure and around 38° C.), and under this condition the gas mist pressure bath is carried out.

The above mentioned explanation has been made to the lower extremities of the human living organism as the example to be performed, and the invention is applicable to various parts for the gas mist pressure bathing. Then, the optimum gas mist pressure bathing is performed by using the shapes of the pressure bathing cover 51 meeting object parts of the living organism.

Figure 7:
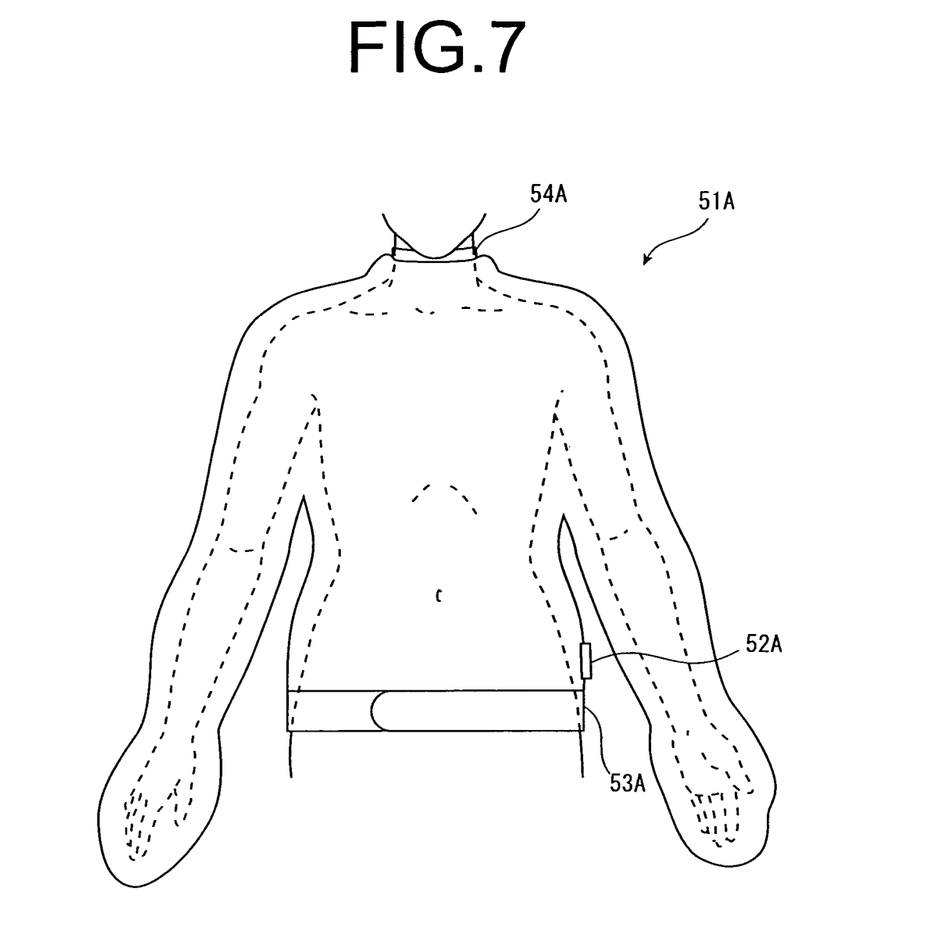
FIG. 7 A typical view showing a configuration example (No. 1) of the pressure bathing cover for the living organism of the gas mist pressure bathing system depending on the invention.
Figure 8:
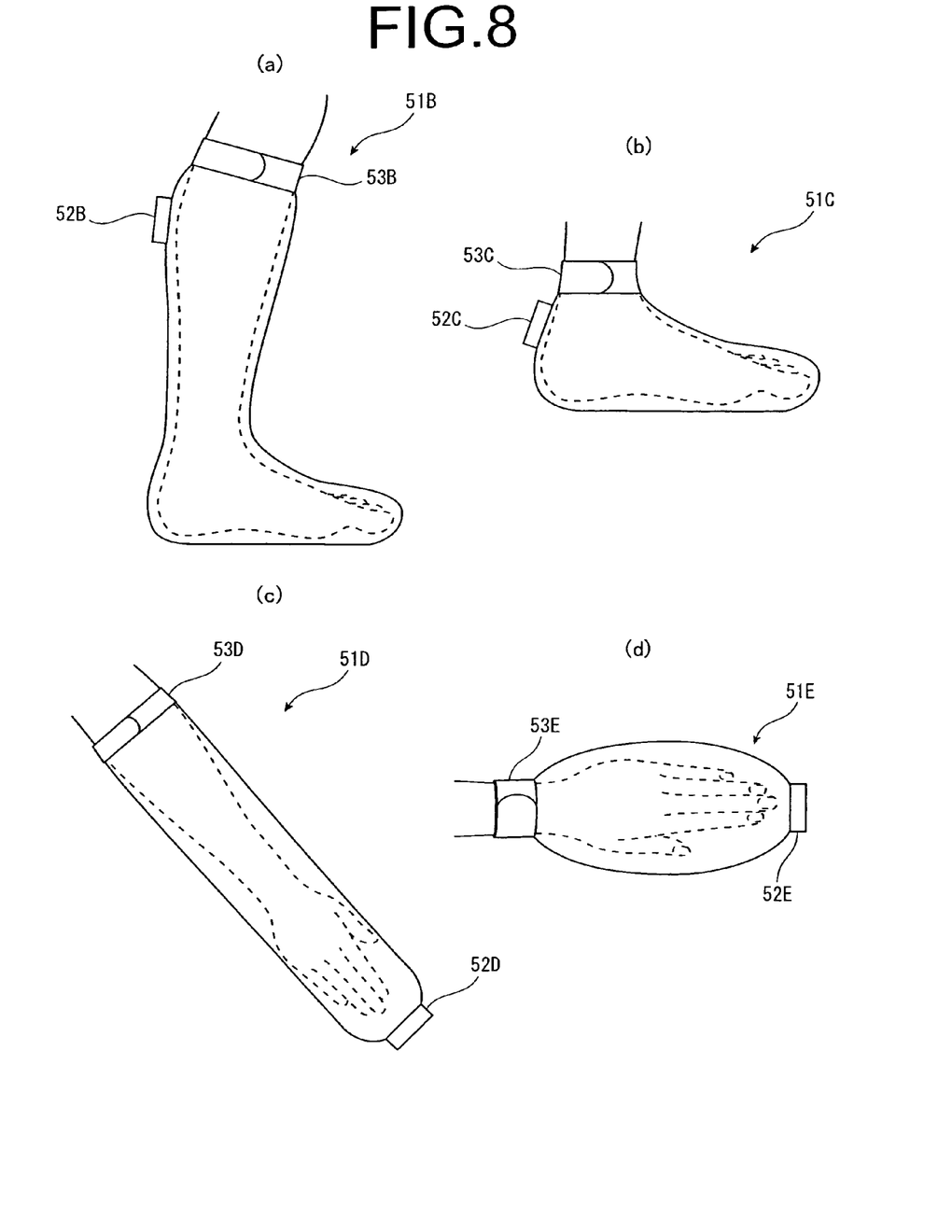
FIG. 8 Typical views showing configuration examples (No. 2) of the pressure bathing covers for the living organism of the gas mist pressure bathing system depending on the invention.
Figure 9:
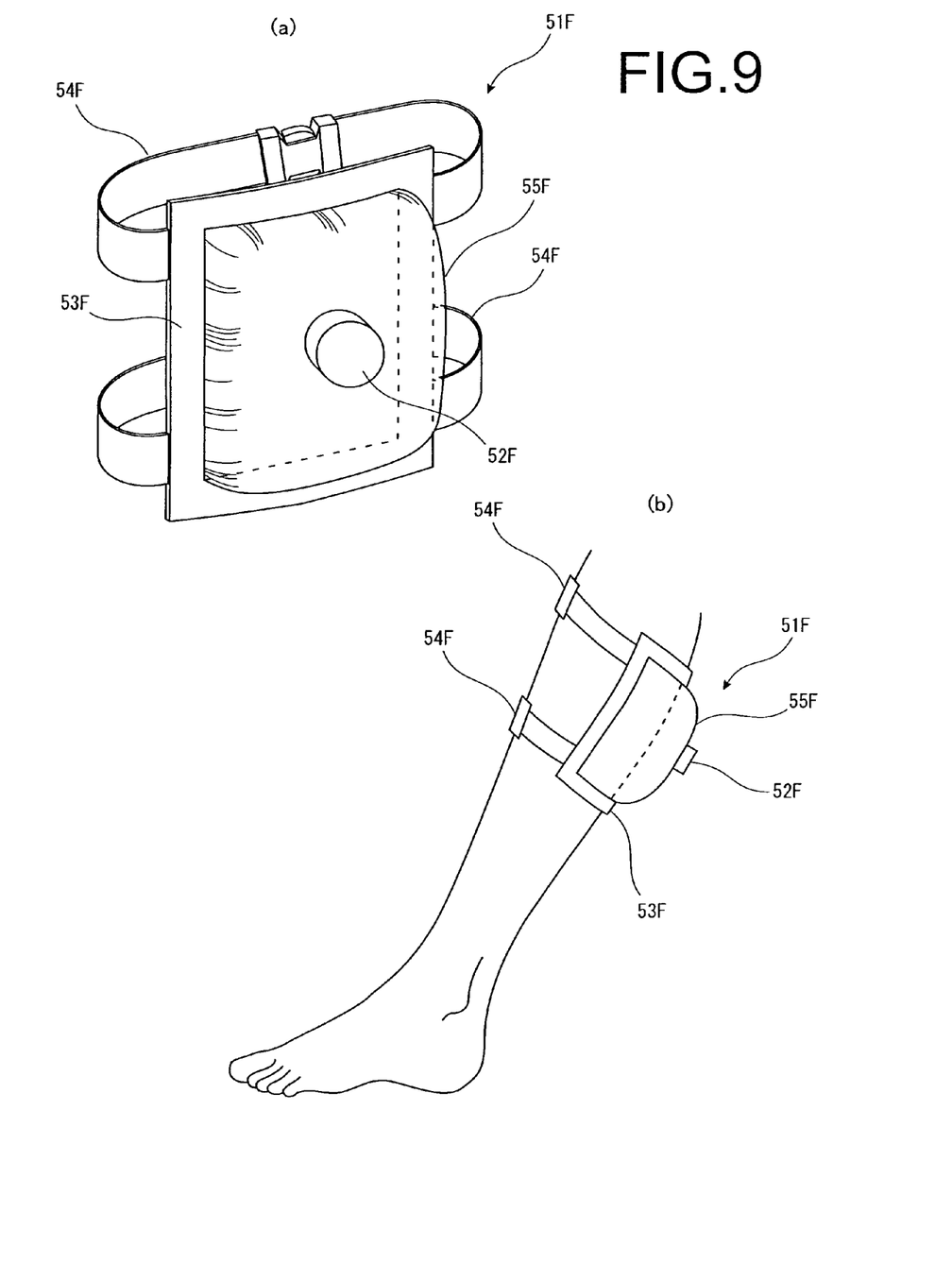
FIG. 9 Typical views showing configuration examples (No. 3) of the pressure bathing covers for the living organism of the OS mist pressure bathing system depending on the invention.

FIGS. 7 to 9 show the various shaped examples of the pressure bathing cover 51 for the living organism. At first, FIG. 7 shows the schematic view of the pressure bathing cover 51A for the upper half of the living organism. The pressure bathing cover 51A has a shape for wrapping the whole of the upper half of the living organism, and has a stopper 53A for attaching to and detaching from the living organism when opening a waist part and stopping leakage of the gas mist. A similar stopper 54A is formed around the opening of a neck. 52A designates a supply inlet for introducing the gas mist inside.

FIG. 8 shows the various shaped examples of the pressure bathing covers 51 for covering further limited parts. FIG. 8(*a*) is the pressure bathing cover 51B for one-side lower extremity (lower part under a knee) of the living organism. The pressure bathing cover 51B has the stopper 53B at its opening part and a supply inlet 52B for introducing inside the gas mist and the gas. FIG. 8(*b*) is the pressure bathing cover 51C for a foot. The pressure bathing cover 51C has a stopper 53C at its opening part and a supply inlet 52C for introducing inside the gas mist. FIG. 8(*c*) is the pressure bathing cover 51D for a forearm. The pressure bathing cover 51C has a stopper 53D at its opening part and a supply inlet 52D for introducing inside the gas mist. FIG. 8(*d*) is the pressure bathing cover 51E for a hand. The pressure bathing cover 51E has a stopper 53E at its opening part and a supply inlet 52E for introducing the gas mist inside thereof.

Further, FIG. 9 shows a patch shaped pressure bathing cover 51F. FIG. 9(*a*) is a view showing the outline of the patch shaped pressure bathing cover 51F. FIG. 9(*b*) is a view showing an external appearance when attaching the patch shaped pressure bathing cover 51F to the living organism (herein, the lower extremity). The pressure bathing cover 51F is composed of a cover part 55F for covering the skin and mucous membrane of the living organism, a stopper 53F provided at the margin of the cover part 55F and directly attached to the skin and mucous membrane, a supply inlet 52F for supplying the gas mist into the space defined by the cover 55F and the stopper 53F, and fasteners 54F made of belts or strings for fastening the cover part 55F to the living organism.

In regard to the pressure bathing cover 51, other than the examples shown in FIGS. 7 to 9, various shapes may be assumed. In sum, if forming the space for sealing inside the gas mist, any shape is sufficient. An air discharge outlet may be formed for exhausting the gas mist from the inside of the pressure bathing cover 51. In addition, the invention may be applied not only to the human living organism but also to animals.

Second Embodiment

Figure 10:
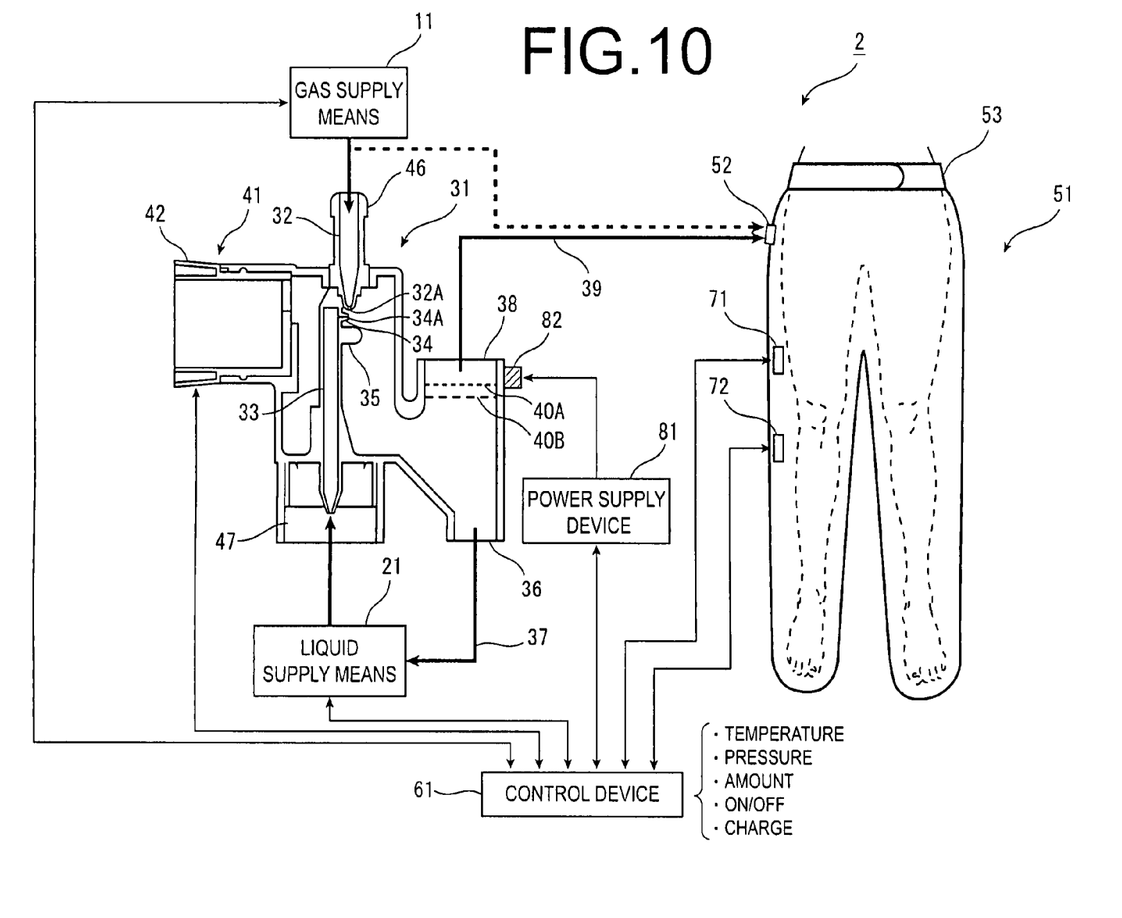
FIG. 10 A generally schematic view of the gas mist pressure bathing system depending on a second embodiment of the invention.

FIG. 10 is the generally schematic view of the gas mist pressure bathing system depending on the second embodiment of this invention. This embodiment will explain the gas mist pressure bathing system further having a means for electrically charging the generated mist. As to the same parts as those of the first embodiment shown in FIG. 1, the same numerals will be given, and detailed explanation will be omitted.

As shown in FIG. 10, the gas mist pressure bathing system 2 of this embodiment is arranged with an electrode 82 at the gas mist discharge outlet 38 of the gas mist supply device 31. The electrode 82 is connected to a power supply device 81, and the control device 61 sets voltage values and performs on-off switch.

The electrode 82 supplies an electric charge (minus charge is desirable) when exhausting the mist generated by the gas mist supply device 31 from the gas mist discharge outlet 38. Thereby, the mist is made charged so that adhesion to a charged material can be heightened. For example, if heightening adhesion to the skin and the mucous membrane of the living organism, an effect of more increasing absorption rate of the gas by the mist is further heightened, and if the mist contains the above mentioned medicines, penetration into the skin and the mucous membrane can be accelerated.

For carrying out the gas mist pressure bathing by using the gas mist pressure bathing system 2 of the present embodiment, the pressure bathing cover 51 is fixedly secured to the living organism (herein, as the example, the lower extremity) and closed. Gas is supplied from the gas supply means 11 into gas mist supply device 31, and is exhausted from the gas nozzle 32. Then, the liquid is sucked up by negative pressure generated owing to air current, reaches the liquid sucking pipe 34 from the liquid nozzle 33, runs against the gas flow at the front end open 34A of the liquid sucking pipe, and collides with the baffle 35. By this collision, the gas mist is generated. The control device 61 performs controls of gas supplying pressure or liquid temperature. If necessary, the regulator 41 is opened and closed to regulate supplying pressure of the gas mist. Further, the control device 61 turns on a power supply device 81 and gives an electric charge to the mist from the electrode 82. A size of the mist then generates is desirably fine, and concretely less than 10 μm is optimum.

The generated gas mist passes through the fine holes of the plates 40A, 40B and reaches the gas mist supply pipe 39 from the gas mist discharge outlet 38. The mist liquefied then is exhausted from the liquid discharge portion 36 into the liquid discharge pipe 37 and is returned the liquid supply means 21. The gas mist having reached the gas mist supply pipe 39 is supplied into the pressure bathing cover 51 for the living organism. At this time, preferably, in the pressure bathing cover 51 for the living organism, the gas is controlled to exist about 95 to 97%, while the liquid is controlled to exist about 3 to 5%. The control device 61 is controlled such that the inside of the pressure bathing cover 51 for the living organism becomes the optimum pressurized and heated conditions (around 1.02 to 2.5 air pressure and around 38° C.), and under this condition the gas mist pressure bathing is carried out.

As having mentioned above, according to the gas mist pressure bathing system, it is possible to control the amount of the gas mist within the pressure bathing cover, pressure and others, so that the gas mist pressure bathing can be always taken under the optimum condition.

Further, pressurization into the pressure bathing cover for the living organism is simplified, and absorption of gas into the living organism (absorption passing through the skin or the mucous membrane) can be more efficiently performed.

The above explanation has been made to the embodiments of the invention, but the invention is not limited thereto, and so far as not deviating from the subject matter of the invention, various kinds of embodiments are, of course, available.

INDUSTRIAL APPLICABILITY

Thus, the present invention relates to the gas mist pressure bathing system, in which the gas mist is directly contacted to the skin or mucous membrane of the living organism at pressure more than the predetermined value, and has an industrial applicability.

REFERENCE SIGNS LIST

1, 2: gas mist pressure bathing system
11: gas supply means
21: liquid supply means
21A: syringe
21B: liquid pack
22A, 22B: liquid storages
23A, 23B: connecting portions
24A, 24B: liquid supply inlets
25: change valve
26: piston
31: gas mist supply device
31A: gas mist supply device main element
32: gas nozzle
32A: front end open of the gas nozzle
33: liquid nozzle
34: liquid sucking pipe
34A: front end open of the liquid sucking nozzle
35: baffle
36: liquid discharge portion
37: liquid discharge pipe
38: gas mist discharge outlet
39: gas mist supply pipe
39A: cornice shaped pipe
40A, 40B: plates
41: regulator
41A: engaging portion
42: rotating part
42A: concave grooved portion
42B: convex portion
43A, 43B: semicircles
44A: path
44B: opening
45: gas storage
46: gas mist supply means joint
47: liquid supply means joint
51: pressure bathing cover for the living organism
52: gas mist supply inlet
53, 54A: stopping parts
54F: holding parts
55F: covering part
61: control device
71: manometer
72: temperature gauge
81: power supply device
82: electrode

The invention claimed is:

1. A gas mist pressure bathing system, for directly contacting a gas mist prepared by pulverizing and dissolving a gas including carbon dioxide, oxygen, or a mixed gas of carbon dioxide and oxygen or air, and a liquid to a skin and mucous membrane of a living organism at a density of not less than a predetermined value, comprising:

a gas supply device for supplying the gas, a liquid supply device for supplying the liquid, a gas mist supply device connected to the gas supply device and the liquid supply device, which sucks up the liquid by a negative pressure owing to gas flow from the gas supply device to collide with the gas for generating and supplying the gas mist prepared by pulverizing and dissolving the gas and the liquid, a living organism covering member which covers the skin and mucous membrane of the living organism and forms a space for sealing the gas mist supplied from the gas mist supply device therein, and a control device, wherein the gas mist supply device has a gas mist supply pressure regulating device for regulating a supply pressure of the gas mist to the living organism covering member, the gas mist supply pressure regulating device includes a base part provided with an engaging hole having an outer opening at an outer end thereof and an inner opening which leads to inside the gas mist supply device, said inner opening being defined by a partial closure plate across the engaging hole and having a flat bottom surface, and also a rotatable cylindrical part having an inlet opening at one end and an outlet opening at another end thereof, said outlet opening being defined by a partial closure plate across the cylindrical part and having a flat outer end surface, the cylindrical part is fittedly received in the engaging hole of the base part to rotate axially therein with the outer end surface of the partial closure plate of the cylindrical part being in contact with the bottom surface of the partial closure plate of the base part, and to enable to communicate an inside and an outside of the gas mist supply device with each other through the inlet opening of the cylindrical part and the inner opening of the base part, and, the control device controls rotation of the cylindrical part within the engaging hole, so as to change a rotational position of the partial closure plate thereof relative to that of the base part, thereby varying an amount of gas, air or gas mist flowing from the outside through the inlet opening and the inner opening into the gas mist supply device to regulate the supply pressure of the gas mist to the living organism covering member.

2. A gas mist pressure bathing system according to claim 1, further comprising a sensor or sensors for measuring supply conditions of the gas, liquid and gas mist, and measured values of the sensor or sensors are fed to the control device for controlling supply of the gas, air and/or gas mist, and/or the rotation of the cylindrical part of the gas mist supply pressure regulating device.

3. A gas mist pressure bathing system according to claim 1, wherein the gas mist supply device includes at least one pored plate placed inside thereof near an outlet to the living organism covering member for refining the gas mist to be supplied thereto, and a liquid discharge portion provided below the outlet to the living organism covering member and connected to the liquid supply device for returning excessive liquid inside the gas mist supply device thereto.

4. A gas mist pressure bathing system according to claim 1, wherein the gas mist supply device includes a vertical gas nozzle connected to the gas supply device at a top end thereof for discharging the gas downward therefrom, and a vertical liquid nozzle connected to the liquid supply device at a bottom end thereof; the liquid nozzle has an upper horizontal liquid sucking pipe with an opening near a discharge opening of the gas nozzle, and a lower baffle projecting to be disposed below the discharge opening of the gas nozzle; and the inner opening of the gas mist supply pressure regulating device is located on an opposite side to an outlet to the living organism covering member with the gas nozzle and the liquid nozzle disposed therebetween.

5. A gas mist pressure bathing system according to claim 3, wherein the gas mist supply device includes two pored plates including an upper plate and a lower plate disposed near and below the outlet to the gas mist supply device and vertically apart from each other, the upper plate has pores of a smaller diameter than that of the lower plate, and the pores of the upper plate and the pores of the lower plate are out of alignment with each other.

6. A gas mist pressure bathing system according to claim 1, wherein the control device controls the rotation of the cylindrical part within the engaging hole of the base part, so that the gas mist is supplied intermittently into the living organism covering member to perform interval pressurization.

7. A gas mist pressure bathing system according to claim 1, wherein the gas mist supply pressure regulating device further includes a gas storage which is connected to the inlet opening of the cylindrical part for supplying gas, air or gas mist contained therein to the gas mist supply device through the inlet opening and the inner opening of the gas mist supply pressure regulating device.

8. A gas mist pressure bathing system according to claim 7, wherein the gas storage is in the shape of a bag formed of a soft material.

9. A gas mist pressure bathing system according to claim 1, wherein the partial closure plate of the rotatable cylindrical part and the partial closure plate of the base part have a semicircular shape, and
the gas mist supply pressure regulating device is structured so that the partial closure plate of the rotatable cylindrical part and the partial closure plate of the base part partially overlaps each other to control the communication between the inside and outside of the gas mist supply device.

* * * * *